(12) United States Patent
Couture (10) Patent No.: US 8,512,346 B2
(45) Date of Patent: Aug. 20, 2013

(54) METHOD AND SYSTEM FOR COMPUTER ASSISTED ORTHOPEDIC KNEE SURGERY

(75) Inventor: Pierre Couture, Montreal (CA)

(73) Assignee: Orthosoft Inc., Montreal (CA)

(\*) Notice: Subject to any disclaimer, the term of this patent is extended or adjusted under 35 U.S.C. 154(b) by 514 days.

(21) Appl. No.: 12/747,297

(22) PCT Filed: Jan. 16, 2009

(86) PCT No.: PCT/CA2009/000049
§ 371 (c)(1),
(2), (4) Date: Jun. 10, 2010

(87) PCT Pub. No.: WO2009/089629
PCT Pub. Date: Jul. 23, 2009

(65) Prior Publication Data
US 2010/0292703 A1    Nov. 18, 2010

Related U.S. Application Data

(60) Provisional application No. 61/021,371, filed on Jan. 16, 2008.

(51) Int. Cl.
*A61B 17/15*    (2006.01)

(52) U.S. Cl.
USPC .............................. 606/88; 606/86 R; 606/96

(58) Field of Classification Search
USPC ............... 600/407, 426–427, 429; 606/86 R, 606/87–89, 96–98, 130
See application file for complete search history.

(56) References Cited

U.S. PATENT DOCUMENTS

| 5,234,433 | A | 8/1993 | Bert et al. |
| 5,395,376 | A | 3/1995 | Caspari et al. |
| 6,450,978 | B1 \* | 9/2002 | Brosseau et al. .............. 600/595 |
| 6,695,848 | B2 | 2/2004 | Haines |
| 6,923,817 | B2 \* | 8/2005 | Carson et al. .................. 606/130 |
| 7,894,872 | B2 \* | 2/2011 | Sherman ........................ 600/407 |
| 7,993,341 | B2 \* | 8/2011 | Grimm et al. ............... 606/86 R |
| 2005/0209605 | A1 | 9/2005 | Grimm et al. |

OTHER PUBLICATIONS

Inernational Search Report of PCT/CA2009/000049, mailing date: May 4, 2009.

\* cited by examiner

*Primary Examiner* — Nicholas Woodall
*Assistant Examiner* — Larry E Waggle, Jr.
(74) *Attorney, Agent, or Firm* — Norton Rose Fulbright Canada LLP (57) ABSTRACT

A method and system (10) for the installation of a cutting guide (60) on a bone element (33) in orthopedic computer assisted surgery is provided. The method includes positioning a drill guide (30) against a distal end of the bone element (33), determining at least two pin locations on one of a medial (31) and a lateral side of the bone element (33), fastening locating pins (42) to the bone element (33) at the determined pin locations, removing the drill guide (30) and installing a CAS bone reference (20) in its place on the same locating pins (42), and subsequently mounting the cutting guide (60) to the same locating pins (42).

22 Claims, 5 Drawing Sheets

FIG_1

METHOD AND SYSTEM FOR COMPUTER ASSISTED ORTHOPEDIC KNEE SURGERY

CROSS-REFERENCE TO RELATED APPLICATIONS

The present application is a national phase entry of international patent application No. PCT/CA2009/00049 filed Jan. 16, 2009, which claims priority on U.S. provisional patent application No. 61/021,371 filed Jan. 16, 2008, the entire content of each which is incorporated herein by reference.

TECHNICAL FIELD

The present application relates generally to a surgical tool and its method of use in orthopedic surgery. More particularly, the present application is directed to an improved system and technique for orthopedic knee surgery using a computer assisted surgery (CAS) system.

BACKGROUND OF THE ART

Computer Assisted Surgery (CAS) systems are increasingly used for orthopedic operations in general, and for joint replacement surgeries in particular, in order to continue to improve the accuracy and long-term success of joint replacement surgery. The accuracy of cuts and drilled holes performed in joint replacement surgeries, such as in knee arthroplasty or total knee replacement (TKR) for example, is of prime importance, such that the installation of the implants can be made such that they best duplicate the kinematics of the natural knee.

Known optical, radio frequency and magnetic based CAS systems employ passive and active trackable elements affixed to objects, such as surgical tools and patient bone references, in order to permit the determination of position and orientation of the objects in three-dimensional space. Preoperatively taken images, computer generated models created from preoperative patient scans or intra operative landmark digitization are some of the methods used to provide accurate patient anatomical information to the CAS system, such that the real-time position of the same anatomical elements can be registered or calibrated and thus tracked by the CAS system, permitting these elements to be displayed to the surgeon in real time and their positions and orientations relative to the surgical tools used during the surgery.

Total knee replacement surgery, for example, typically requires one or more precise cuts to be made in the femur and/or tibia, such that the implant correctly fits and best replicates the geometry of a natural healthy knee. To perform these steps, in both conventional and CAS total knee replacement surgeries, it is known to use a tool or implement known as a surgical tool guide block which provides a drill and/or cutting guide to assist the surgeon when performing the steps required to prepare the femur and/or tibia for receiving the corresponding implant, including making a distal cut(s) in the femur.

Known TKR procedures include creating a distal cut in the femur such as to resect enough bone to permit the installation of the femoral implant. In conventional (i.e. non computer assisted) total knee replacement surgery, a distal cutting block is typically positioned and aligned by the surgeon and pinned in place on the anterior surface of the femur such that a cutting slot in the distal cutting block is aligned in the correct location for the distal cut. In CAS total knee replacement, it is also known to use a distal pin drill guide to accurately create pin holes in the distal end of the femur into which locating pins are inserted and employed to fix the distal cutting guide, either integrally formed with the distal pin drill guide or being a separate element, in the correct location to make the distal cut in the femur. Generally, the distal drill/cutting guide member comprises part of an assembly including an anterior guiding platform, that is fixed relative to the femur and on which the drill/cutting guide is displaceable by a selected, measurable amount to locate the drill/cutting guide in a desired position relative to the anterior guiding platform and therefore relative to the distal end of the femur. A tracked guide block is often intramedullarly fastened to the femur, and the anterior guiding platform can then be engaged thereto. Depending on the type of implant being used, and once aligned with the most distal femoral condyle, the drill/cutting guide can then be proximally displaced on the fixed anterior guiding platform by a selected amount corresponding to the amount of bone to be resected.

Therefore, the distally-mounted positioning block is fixed to the distal end of the femur using a bone screw or pins, and once the determined position for the cutting guide block has been established using this positioning block, the cutting block itself is then pinned directly in place on the bone, thereby requiring more drilled holes and additional pins inserted into the bone. The positioning block is typically then removed, leaving the cutting guide block pinned in place on the bone such as to be then able to make the necessary distal resection cut.

While this method has proven effective to date, there exits a need to reduce the invasiveness of TKR procedures such that less drilling, screwing and/or pinning directly into the bone, particularly on the distal end of the femur, is required.

SUMMARY

It is therefore an object of the invention to provide an improved system and method of using a cutting guide block in orthopedic knee surgery.

There is provided, in accordance with an aspect of the present invention, a method of installing a cutting guide on a bone element in orthopedic computer assisted surgery, the method comprising: providing a computer assisted surgery (CAS) system; positioning a drill guide against a distal end of the bone element; determining at least two pin locations on one of a medial and a lateral side of the bone element; fastening locating pins to the bone element at said determined pin locations; removing the drill guide and installing a CAS bone reference in its place on the locating pins, thereby engaging the bone reference to the bone element, the CAS bone reference having a trackable member thereon which is locatable and trackable in three dimensional space by the CAS system; digitizing landmarks on an outer surface of the bone element such that the CAS system generates a bone model representative of and registered to the bone element, such as to enable the CAS system to track the position and orientation in space of the bone element in view of the relative positions of the digitized landmarks and the bone reference fixed to the bone element; and mounting the cutting guide to the locating pins, the cutting guide including at least a distal cutting guide portion disposed at a determined resection distance relative to the bone element.

There is also provided, in accordance with another aspect of the present invention, a method of preparing a femur for total knee replacement surgery using a computer assisted surgery (CAS) system, the method comprising: installing at least two locating pins in a distal end of the femur at positions disposed outside a region of the femur to be resected; engaging a bone reference which is in communication with the CAS system to the locating pins; digitizing a number of landmarks on an outer surface of the femur using a digitizing pointer in communication with the CAS system; and mounting a cutting guide to the locating pins, the cutting guide including at least a distal cutting guide disposed at a determined distal resection distance relative to a distal end of the femur.

There is also provided, in accordance with another aspect of the present invention, a system for conducting orthopedic surgery on a bone element comprising: a computer assisted surgery (CAS) system including a computer, a display device in communication with the computer, and a tracking system also in communication with the computer; a drill guide having at least two substantially perpendicular abutment surfaces thereon which are adapted to be abutted against the bone element, at least two guide holes extend through the drill guide and are located therein at positions disposed outside a predetermined region of the bone element when said abutting surfaces are in contact with their respective surfaces of the bone element, said guide holes being sized to accommodate the insertion of locating pins therethrough, the predetermined region being a portion of the bone element that is to be resected; a bone reference having a first pair of holes therein which mate with said locating pins such as to engage the bone reference to said locating pins, the bone reference having a first trackable member thereon which is locatable and trackable in three dimensional space by the CAS system; and a cutting guide having a second pair of holes therein which mate with said locating pins such as to engage the cutting guide to said locating pins, the cutting guide including at least a distal cutting guide portion disposed at a determined resection distance relative to the bone element which is determined by the CAS system.

There is further provided, in accordance with yet another aspect of the present invention, a kit for conducting knee replacement surgery on a bone element of a knee using a computer assisted surgery (CAS) system, comprising: at least two locating pins adapted to be fixed to the bone element; a drill guide having a distal abutment surface and a proximal abutment surface respectively adapted to be abutted against a most distal and a most proximal surface of the bone element, the drill guide having at least one of a medial and a lateral projection which respectively include medial and lateral abutment surfaces, and wherein at least two guide holes extend through said projection and are disposed therein at positions located outside a predetermined region when said abutting surfaces are in contact with their respective surfaces of the bone element, said guide holes being sized to receive locating pins therethrough for fixation to the bone element, the predetermined region being a portion of the bone element that is to be resected; a bone reference having a first pair of holes therein which mate with said locating pins such as to engage the bone reference to said locating pins, the bone reference having a first trackable member thereon which is locatable and trackable in three dimensional space by the CAS system; and a cutting guide having a base portion with a second pair of holes therein which mate with said locating pins such as to engage the cutting guide to said locating pins, the cutting guide including at least a distal cutting guide portion engaged with the base portion and disposed at a determined resection distance relative said base portion and to said locating pins, and therefore relative to the bone element to which the locating pins are adapted to be fixed.

BRIEF DESCRIPTION OF THE DRAWINGS

Further features and advantages of the present invention will become apparent from the following detailed description, taken in combination with the appended drawings, in which.

DETAILED DESCRIPTION OF A PREFERRED EMBODIMENT

Figure 1:
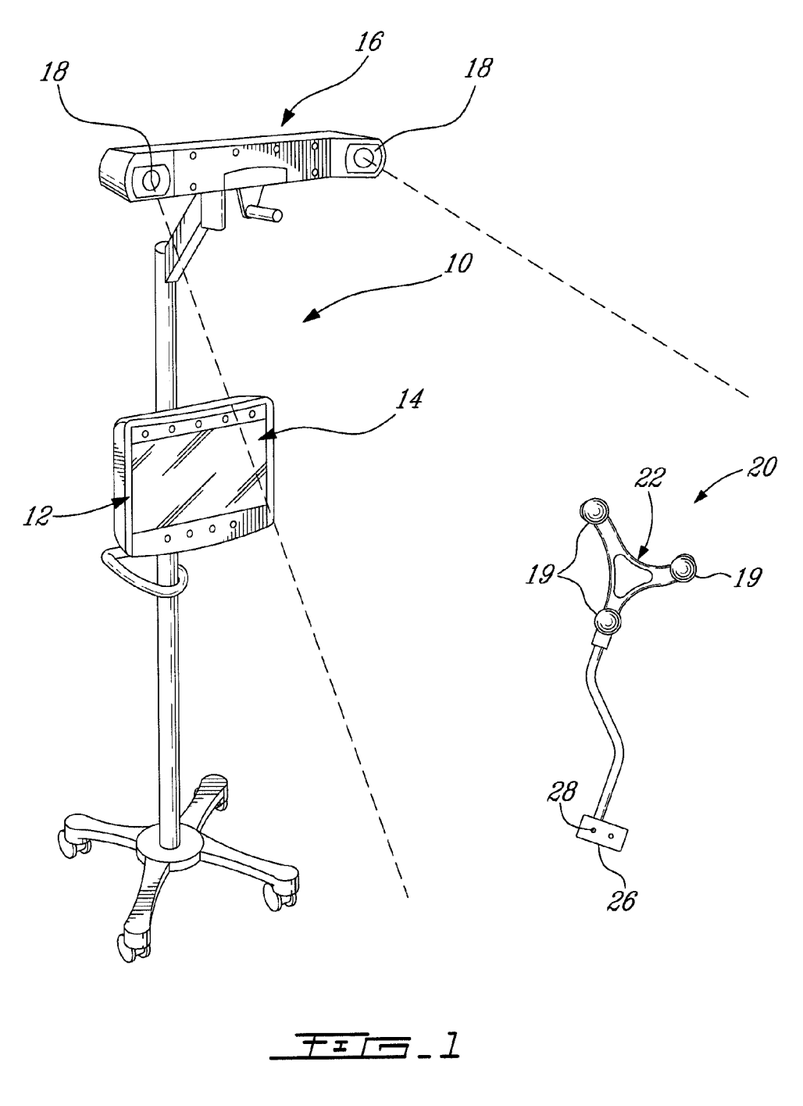
FIG. 1 is a perspective view of a Computer Assisted Surgery (CAS) system and tracked bone reference used in conjunction therewith.

Referring to FIG. 1, the computer assisted surgery (CAS) system 10 is used for orthopedic surgery, and in the present embodiment the system is particularly employed for conducting total knee replacement (TKR) surgery. The CAS system 10 is capable of real time location and tracking of a plurality of trackable members in a surgical field, each having a distinctive set of identifiable markers thereon. These trackable members are thus affixed both to the surgical tools employed with the system 10 and to the bone elements undergoing surgery.

The CAS system 10 generally includes at least a computer 12, a display device 14 in communication with the computer, and a tracking system 16 also in communication with the computer. The tracking system 16 may be an optical tracking system, using infra-red cameras 18 for example, however any other type of tracking system can also be used, such as ones which employ laser, ultrasound, electromagnetic or RF waves for example, to locate the position of the identifiable markers of tracking members within range of the sensing devices of the system.

The CAS system 10 is capable of depicting a bone reference 20, a digitizer and any other surgical tools which may be required, on the display device 14 (which may include a monitor for example) relative to the patient anatomy, including the pertinent bones which are also tracked in real time by the system. The CAS system 10 is preferably a CT-less system.

A bone reference 20 is used in conjunction with the CAS system 10. The bone reference 20 includes a tracking member 22 having at least three retro-reflective identifiable markers 19 thereon such that the tracking member 22 is locatable and trackable by the tracking system 16 of the CAS system 10. The CAS system 10 is thus able to determine the position, orientation and movement of the tracking member 22 (and therefore also the bone element to which the bone reference 20 is fastened) in three dimensional space and in real time. The retro-reflective identifiable markers 19 of the trackable member 22 can be removably engaged to either side or both sides of the tracking member 22 of the bone reference 20, such that the best visual contact between the detectable markers 19 and the cameras 18 of the CAS system 10 is ensured. Therefore, regardless of which knee is being operated on, the tracking member 22 will be readily visible and detected by the tracking system.

A block portion 26 is fixed to one end of the bone reference 20, and includes a pair of holes 28 therethrough which are adapted to mate with corresponding pins that are fixed to the femur, in accordance with the method which will be described in further detail below. As will be seen, these pins are the same ones used to locate the cutting guide used to create a cut in the bone. Accordingly, by engaging the bone reference 20 to the bone element (such as the femur) using such locating pins, the bone element can be tracked in space using the CAS system 10.

Referring now to FIGS. 2-5, the present system and method for preparing and conducting a distal resection of a knee bone element in preparation of the installation of an implant in a TKR operation will be described. Although the embodiment described below is described with regard to a femur, it is to be understood that the present method can also be adapted and employed at least on a tibia.

Figure 2:
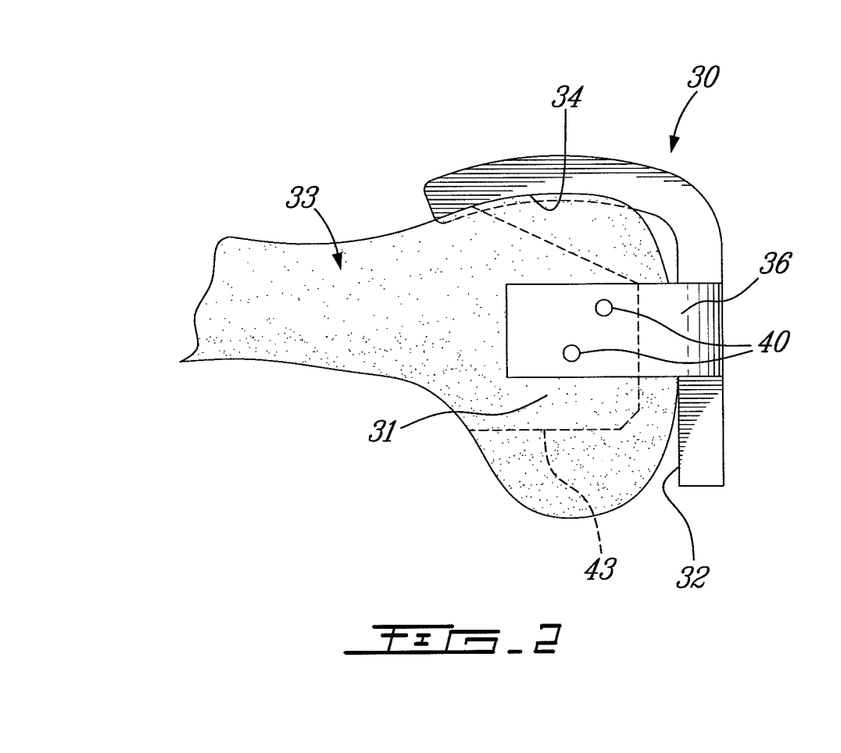
FIG. 2 is a side elevation view of a drill guide mounted on the distal end of a femur.
Figure 3:
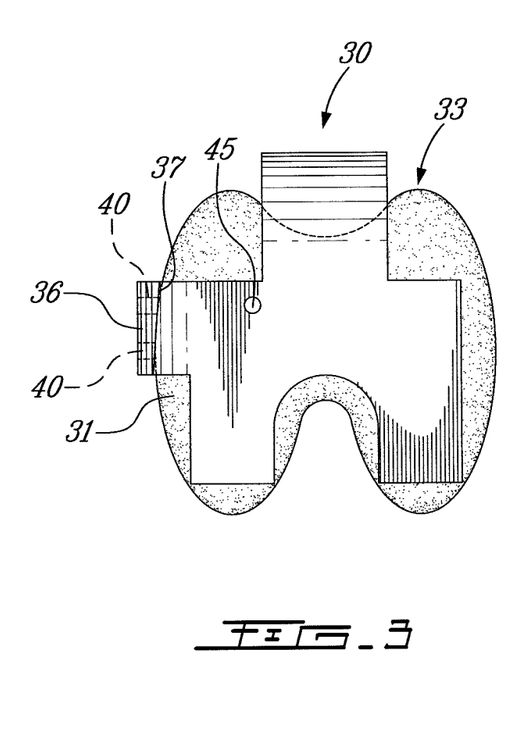
FIG. 3 is an end view of the drill guide and femur of FIG. 2.

As seen in FIGS. 2 and 3, a drill guide 30 is used in order to install two locating pins on the medial aspect 31 of the distal end of the femur 33. The drill guide 30 is first installed in place on the femur by abutting a distal abutment surface 32 of the drill guide 30 against the most distal point on the femur and by abutting a proximal abutment surface 34 of the drill guide 30 against the most proximal point on the femur. A medial projection 36 of the drill guide 30 protrudes from the side of the guide 30, and a medial abutment surface 37 thereon is also brought into abutment with the most medial point of the femur. Once all three of these abutting surfaces 32, 34, 37 are simultaneously in abutment with the distal end of the femur 33, the drill guide is held in position and two holes are drilled in the medial aspect 31 of the femur 33 using the drilling guide holes 40 defined in the medial projection 36 of the drill guide 30. An additional, distally positioned, drilling guide hole 45 may also be provided in the guide block 30, for making distally directed holes in the femur if necessary. Two locating pins 42 (see FIG. 4) are then inserted in place within the drilled holes in the femur, via the drilling guide holes 40 of the drill guide 30. In other words, once the holes have been drilled in the femur using the guide holes 40, the locating pins 42 are subsequently inserted through these guide holes 40 and into the holes formed in the bone. The drill guide 30 can then be removed from contact with the femur.

Although the locating pins 42 are installed on the medial side of the bone element (ex: femur) in the embodiment described and depicted, it is to be understood that the drill guide 30 can also be configured such that these pins 42 may be alternately installed in the opposite (lateral) side of the same bone element. For example, the drill guide 30 can include only a lateral projection, having a lateral abutment surface thereon, which corresponds to the medial projection 36 described above. Further still, the drill guide 30 may comprise projections on both the medial and lateral side of the guide, such that the surgeon can select a most appropriate side of the bone element for the drilling and installation of the locating pins. In one embodiment where both medial and lateral projections are disposed on the drill guide, at least one of these projections is displaceable relative to a medial-lateral axis, such as to be able to accommodate knee joints of various sizes. Alternately, drill guides of different sizes can be made available such that one having a most appropriate size given the particular patient's bone geometry can be selected by the surgeon.

With the locating pins 42 in place on the medial side 31 of the femur 33, the drill guide 30 is then removed from abutment with the femur. The size and shape of the drill guide 30, and particularly the medial projection portion 36 thereof, is such that the locating pins 42 are disposed in the femur at locations which avoid or clear the location of the cuts (i.e. box-cut) required to be carried out on the femur to be able to install a femoral implant of any size. For example, the location of cuts to be performed are depicted using broken lines 43 in FIG. 2.

Figure 4:
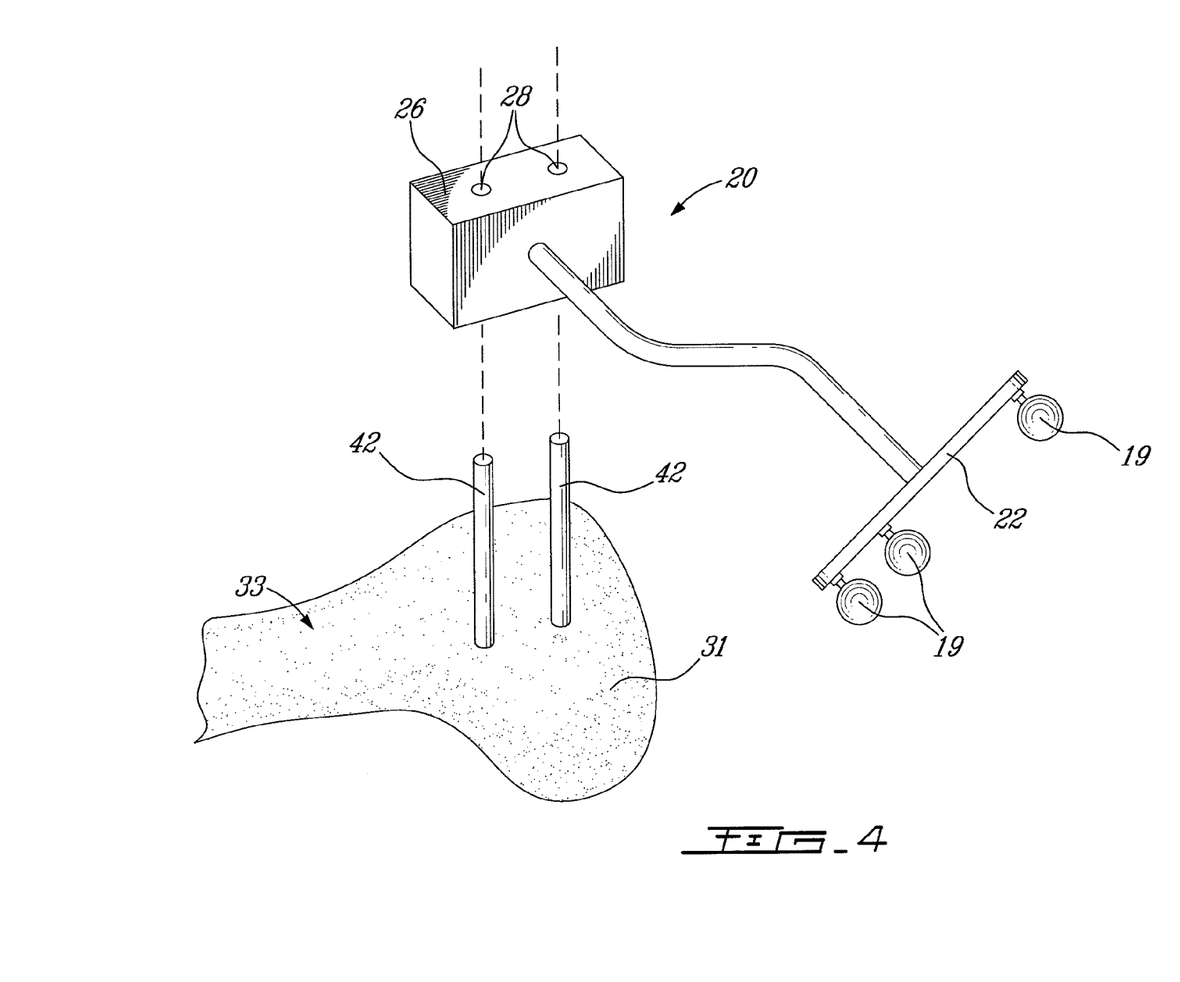
FIG. 4 is a perspective view of the bone reference of FIG. 1 engaging locating pins fixed to a medial aspect of the femur.

Referring to FIG. 4, once the medially mounted locating pins 42 are installed in place on the medial aspect 31 of the femur 33, the bone reference 20 as described above with respect to FIG. 1 is then engaged to the pins 42 by aligning the holes 28 in the block portion 26 of the bone reference 20 with the pins 42, and then sliding the block 26 down the pins until the block 26 abuts the femur. The bone reference 20 is thus securely fixed in place on the femur 33.

Figure 5:
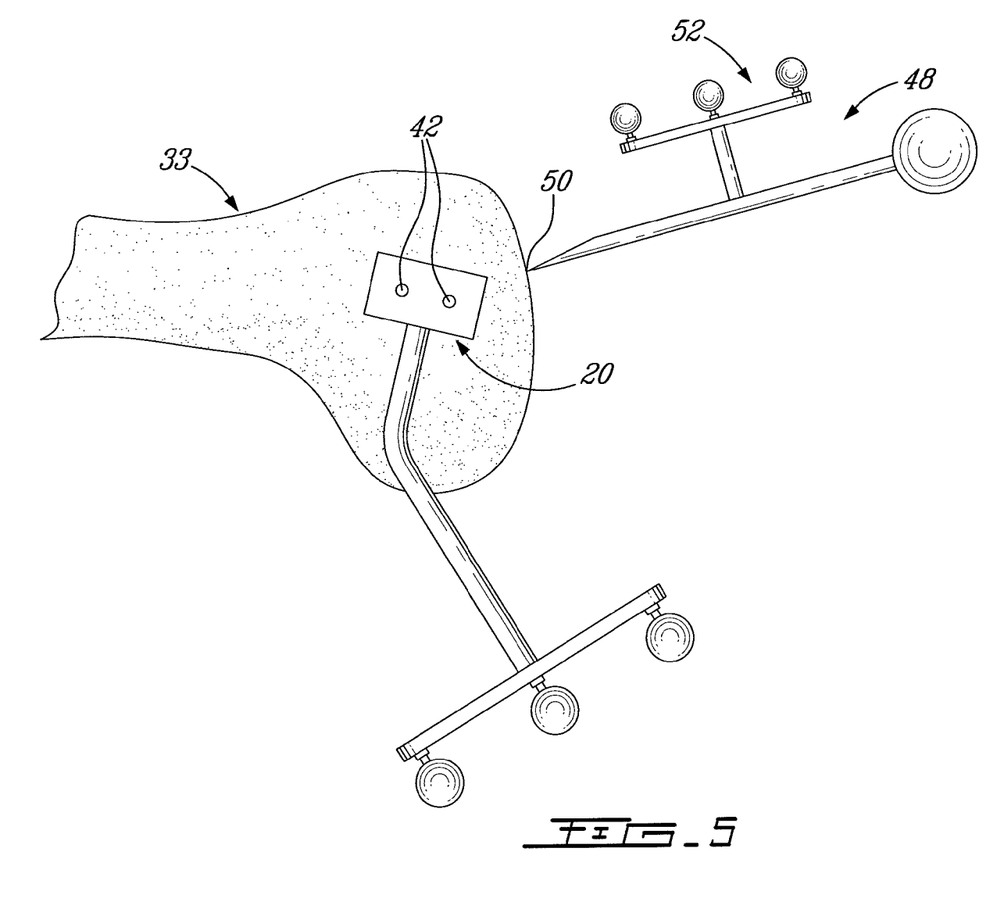
FIG. 5 is a side elevation view of the femur having the bone reference mounted thereto and a CAS digitizing pointer used to digitize surface points on the femur.

As seen in FIG. 5, once the bone reference 20 is secured to the femur 33, a digitizing pointer 48 is then used to digitize a number of landmarks on the surface of the femur. During CT-less knee surgery, only certain portions of the femur can be digitized in order to determine essential information. For example, the longitudinal mechanical axis of the femur can be determined, either with or without digitization. In the present embodiment, at least the most distal portion of the femur's articular surfaces are digitized. The most distal portion of the femur's articular surface (i.e. on the condyles) is particularly important when it is being used to reference specific bone cuts. Alternately, however, the femur can also be fully "constructed" by the CAS system 10 such that the bone model is as accurate as possible to the anatomy of the bone. While several techniques exist to do this, this can be done using surface model reconstruction, which allows the user to digitize small surfaces (i.e. landmarks) instead of individual points only. When each digitized surface has been registered, an approximate model is displayed on the display device 14 of the CAS system 10. Using this method, the computer femur model is thus formed as a mosaic of digitized surfaces. This reconstruction is done in real time, intra-operatively. Regardless of which of these techniques is employed, the digitizing pointer 48, or suitable alternate registration tool, is used to acquire several points and/or larger surfaces on the femur 33, such that these surfaces are digitized to form the virtual bone model, and which is therefore registered (i.e. the location of the surfaces on the actual bone are matched to the bone model created in the CAS system). Given that the tip 50 of the digitizing tool 48 is located at a known position from the tracker 52 thereof, the digitizing pointer permits the CAS system 10 to identify the position in space of any point on the surface of the femur to which the tip 50 is abutted (the point being said to be "digitized"). Accordingly, once enough of these points and/or surfaces have been digitized in order for the system to generate a surface map of the bone, the CAS system 10 is then able to track the position in space of the femur 33 in view of the relative positions of these digitized landmarks and the bone reference 20 fixed thereto. As such, once these points on the femur have been digitized using the digitizer 38, the femur 33 can then be located and tracked in real time and in three dimensions by the CAS system 10.

Figure 6:
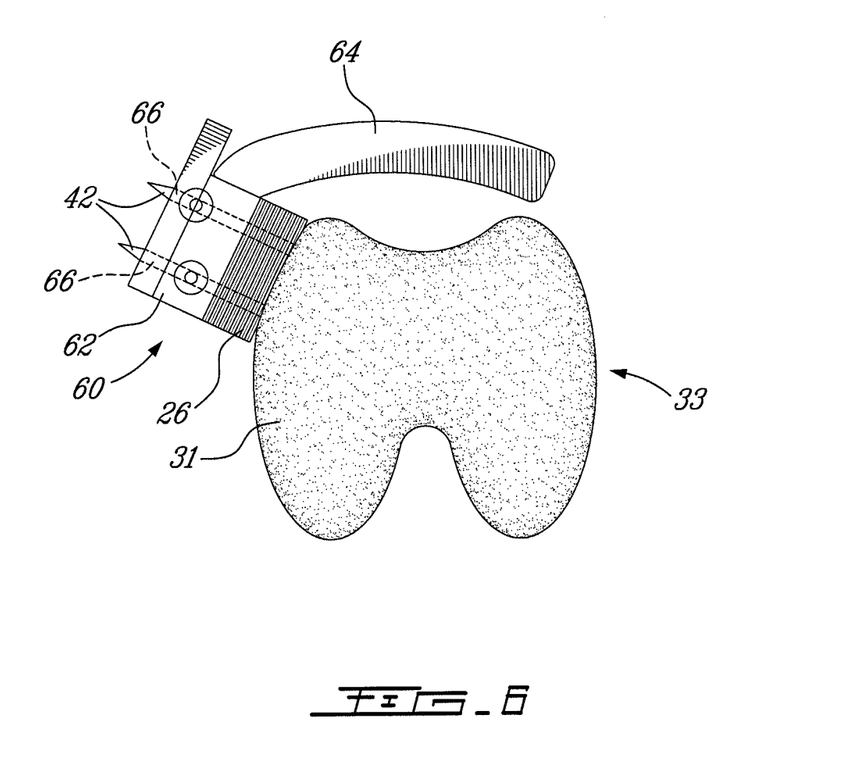
FIG. 6 is an end view of a cutting guide mounted to the femur on the same locating pins previously used to mount the bone reference.

As seen in FIG. 6, once these steps have been completed, a cutting guide 60 is installed onto the same locating pins 42 disposed on the medial side 31 of the distal femur 33, overtop of the base block 26 of the bone reference 20. The cutting guide 60 includes, in at least one embodiment, a base portion 62 to which is engaged a laterally-projecting cutting guide portion 64. At least the base portion 62 defines a pair of holes 66 therethrough, which correspond to and are adapted to receive therein the locating pins 42 fixed to the medial side 31 of the femur 33. As such, this base portion 62 is mounted onto the pins 42, overtop of the base block 26 of the bone reference 20. In the present embodiment, the base portion 62 of the cutting guide 60 is releasably engaged with the block 26 of the bone reference, such as by screw, cam or other suitable releasable fastening mechanism. The geometry of the base portion 62 of the cutting guide 60 is designed in at least one embodiment to locate the distal cutting guide portion 64 at the right position to allow for the predetermined amount of distal resection (ex: 10 mm) for the distal cut to be made in the femur. Alternately, the cutting guide 60, and more specifically the base portion 62 thereof, allows for adjustment of the position of the cutting guide portion 64 relative to the distal end of the femur 33, such as to permit the user (ex: surgeon) to locate the cutting guide portion 64 at a desired position to allow for the necessary amount of resection and/or the desired location and angle of the cut to be performed. In one particular embodiment of the present invention, the base portion 62 of the cutting guide 60 comprises the Ice-Cube™ block made by Zimmer Inc.

In order to perform the distal resection cut using the cutting guide portion 64 of the cutting guide 60, the distal cutting guide portion 64 may be pinned in place on the femur, after the necessary adjustments have been made using the adjustable base portion 62. The cutting guide 60 however preferably remains in place on the femur until after the distal resection cut is made.

Accordingly, using the above-described method and system, no distally-mounted cutting guide block, adjustment block, or other device is required. This permits the reduction in both the surgical time required and the potential invasive impact to the bone element, thereby potentially improving the overall efficiency (and therefore cost) of the TKR operation as well the overall satisfaction of the patient.

The embodiments of the invention described above are intended to be exemplary. Those skilled in the art will therefore appreciate that the forgoing description is illustrative only, and that various alternatives and modifications can be devised without departing from the spirit of the present invention. For example, although particularly described with respect to use of the present system and method for knee surgery, such as total knee replacement (TKR) surgery for example, it is to be understood that this system and method can similarly be used for other types of orthopedic surgery, including but not limited to joint replacements. Accordingly, the present is intended to embrace all such alternatives, modifications and variances which fall within the scope of the appended claims.

The invention claimed is:

1. A method of installing a cutting guide on a bone element in orthopedic computer assisted surgery, the method comprising:
   providing a computer assisted surgery (CAS) system;
   positioning a drill guide against a distal end of the bone element;
   determining at least two pin locations on one of a medial and a lateral side of the bone element;
   fastening locating pins to the bone element at said determined pin locations;
   removing the drill guide and installing a CAS bone reference in its place on the locating pins, thereby engaging the bone reference to the bone element, the CAS bone reference having a trackable member thereon which is locatable and trackable in three dimensional space by the CAS system;
   digitizing landmarks on an outer surface of the bone element such that the CAS system generates a bone model representative of and registered to the bone element, such as to enable the CAS system to track the position and orientation in space of the bone element in view of the relative positions of the digitized landmarks and the bone reference fixed to the bone element; and
   mounting the cutting guide to the locating pins, the cutting guide including at least a distal cutting guide portion disposed at a determined resection distance relative to the bone element.

2. The method of claim 1, wherein the step of positioning further comprises abutting three abutting surfaces of the drill guide against bone element, the abutting surfaces including a distal abutting surface, an anterior abutting surface and at least one of a medial and a lateral abutting surface, each for abutment against a respective surface of the bone element.

3. The method of claim 1, wherein the step of digitizing further comprises using a digitizing pointer in communication with the CAS system to digitize the landmarks on the bone element.

4. The method of claim 1, wherein the step of mounting the cutting guide includes releasably fastening at least a portion of the cutting guide to the CAS bone reference.

5. The method of claim 1, wherein the step of determining the at least two pin locations includes using guide holes formed in the drill guide.

6. The method of claim 5, further comprising positioning the guide holes in the drill guide at predetermined locations relative to at least a distal abutting surface and an anterior abutting surface thereof.

7. The method of claim 5, further comprising selecting predetermined locations of the guide holes such that they are positioned, when the drill guide is positioned in place against a distal end of the bone element, outside a region of the bone element which is to be resected during the orthopedic knee surgery.

8. The method of claim 1, wherein the step of fastening the locating pins further comprises: using the drill guide to drill holes in the bone element at the determined pin locations; and inserting the locating pins into the drilled holes formed in the bone element.

9. A method of preparing a femur for total knee replacement surgery using a computer assisted surgery (CAS) system, the method comprising:
   installing at least two locating pins in a distal end of the femur at positions disposed outside a region of the femur to be resected, including positioning a drill guide against the distal end of the femur, using the drill guide to determine at least two pin locations on one of a medial side and a lateral side of the distal end of the femur and forming holes in the femur at said pin locations within which the locating pins are inserted;
   engaging a bone reference which is in communication with the CAS system to the locating pins;
   digitizing a number of landmarks on an outer surface of the femur using a digitizing pointer in communication with the CAS system; and
   mounting a cutting guide to the locating pins, the cutting guide including at least a distal cutting guide disposed at a determined distal resection distance relative to a distal end of the femur.

10. The method of claim 9, wherein the step of positioning further comprises abutting three abutting surfaces of the drill guide against the femur, the abutting surfaces including a distal abutting surface, an anterior abutting surface and at least one of a medial and a lateral abutting surface, each respectively abutting against a corresponding surface of the femur.

11. The method of claim 9, wherein the step of mounting the cutting guide includes releasably fastening at least a portion of the cutting guide to the bone reference.

12. The method of claim 9, wherein the step of determining the at least two pin locations includes using guide holes formed in the drill guide.

13. A system for conducting orthopedic surgery on a bone element comprising:
- a computer assisted surgery (CAS) system including a computer, a display device in communication with the computer, and a tracking system also in communication with the computer;
- a drill guide having at least two substantially perpendicular abutment surfaces thereon which are adapted to be abutted against the bone element, at least two guide holes extend through the drill guide and are located therein at positions disposed outside a predetermined region of the bone element when said abutting surfaces are in contact with their respective surfaces of the bone element, said guide holes being sized to accommodate the insertion of locating pins therethrough, the predetermined region being a portion of the bone element that is to be resected;
- a bone reference having a first pair of holes therein which mate with said locating pins such as to engage the bone reference to said locating pins, the bone reference having a first trackable member thereon which is locatable and trackable in three dimensional space by the CAS system; and
- a cutting guide having a second pair of holes therein which mate with said locating pins such as to engage the cutting guide to said locating pins, the cutting guide including at least a distal cutting guide portion disposed at a determined resection distance relative to the bone element which is determined by the CAS system.

14. The system as defined in claim 13, further comprising a digitizer having a second trackable member thereon which is independently locatable and trackable in three dimensional space by the CAS system, the digitizer having a tip in known position relative to the second trackable member, the tip of the digitizer being adapted to be used to digitize landmarks on the bone element, the CAS system generating a bone model representative of, and registered to, the bone element such as to enable the CAS system to track the position and orientation of the bone element.

15. The system as defined in claim 13, wherein the cutting guide is un-tracked by the CAS system.

16. The system as defined in claim 13, wherein the abutment surfaces of the drill guide include a distal abutment surface and a proximal abutment surface respectively adapted to be abutted against a most distal and a most proximal surface of the bone element.

17. The system as defined in claim 16, wherein the drill guide includes a projection on at least one of medial and lateral sides thereof which respectively include a medial and lateral abutment surface thereon, and wherein the at least two guide holes extend through said projection.

18. The system as defined in claim 13, further comprising a digitizing pointer in communication with the CAS system, the digitizing point being operable to digitize landmarks on the bone element such that the CAS system generates a bone model representative of, and registered to, the bone element.

19. A kit for conducting knee replacement surgery on a bone element of a knee using a computer assisted surgery (CAS) system, comprising:
- at least two locating pins adapted to be fixed to the bone element;
- a drill guide having a distal abutment surface and a proximal abutment surface respectively adapted to be abutted against a most distal and a most proximal surface of the bone element, the drill guide having at least one of a medial and a lateral projection which respectively include medial and lateral abutment surfaces, and wherein at least two guide holes extend through said projection and are disposed therein at positions located outside a predetermined region when said abutting surfaces are in contact with their respective surfaces of the bone element, said guide holes being sized to receive locating pins therethrough for fixation to the bone element, the predetermined region being a portion of the bone element that is to be resected;
- a bone reference having a first pair of holes therein which mate with said locating pins such as to engage the bone reference to said locating pins, the bone reference having a first trackable member thereon which is locatable and trackable in three dimensional space by the CAS system; and
- a cutting guide having a base portion with a second pair of holes therein which mate with said locating pins such as to engage the cutting guide to said locating pins, the cutting guide including at least a distal cutting guide portion engaged with the base portion and disposed at a determined resection distance relative said base portion and to said locating pins, and therefore relative to the bone element to which the locating pins are adapted to be fixed.

20. The kit as defined in claim 19, wherein the cutting guide is un-tracked by the CAS system.

21. The kit as defined in claim 19, wherein the computer assisted surgery (CAS) system includes a computer, a display device in communication with the computer, and a tracking system also in communication with the computer, the tracking system being operable to locate and track the first and second trackable members.

22. The kit as defined in claim 19, further comprising a digitizing pointer in communication with the CAS system, the digitizing point being operable to digitize landmarks on the bone element such that the CAS system generates a bone model representative of, and registered to, the bone element.

* * * * *